(12) United States Patent
Asaad et al.

(10) Patent No.: US 8,221,466 B2
(45) Date of Patent: Jul. 17, 2012

(54) TRANSCONNECTOR FOR COUPLING FIRST AND SECOND SPINAL FIXATION ELEMENTS

(75) Inventors: Wagdy W. Asaad, Oak Brook, IL (US); Steven E. Mather, Hinsdale, IL (US)

(73) Assignee: Spinecraft, LLC, Westchester, IL (US)

( * ) Notice: Subject to any disclaimer, the term of this patent is extended or adjusted under 35 U.S.C. 154(b) by 236 days.

(21) Appl. No.: 12/646,571

(22) Filed: Dec. 23, 2009

(65) Prior Publication Data

US 2011/0152934 A1    Jun. 23, 2011

(51) Int. Cl.
*A61B 17/70* (2006.01)

(52) U.S. Cl. .................... 606/252; 606/250; 606/251

(58) Field of Classification Search .............. 606/246, 606/250–253
See application file for complete search history.

(56) References Cited

U.S. PATENT DOCUMENTS

| | | | |
|---|---|---|---|
| 4,474,046 A * | 10/1984 | Cook | 72/409.16 |
| 5,944,720 A * | 8/1999 | Lipton | 606/276 |
| 6,234,705 B1 | 5/2001 | Troxell | |
| 6,306,137 B2 | 10/2001 | Troxell | |
| 6,736,817 B2 | 5/2004 | Troxell | |
| 2001/0005468 A1 | 6/2001 | Troxell | |
| 2001/0047171 A1 | 11/2001 | Troxell et al. | |
| 2004/0116928 A1 * | 6/2004 | Young et al. | 606/61 |
| 2004/0133203 A1 * | 7/2004 | Young et al. | 606/61 |
| 2004/0176765 A1 | 9/2004 | Troxell et al. | |
| 2005/0080416 A1 | 4/2005 | Ryan et al. | |
| 2007/0173829 A1 * | 7/2007 | Drewry et al. | 606/61 |
| 2011/0245873 A1 * | 10/2011 | Winslow et al. | 606/254 |

OTHER PUBLICATIONS

SpineCraft Design for Spine Professionnals, 2007.

* cited by examiner

*Primary Examiner* — Eduardo C Robert
*Assistant Examiner* — Ellen C Hammond
(74) *Attorney, Agent, or Firm* — Alan W. Cannon

(57) ABSTRACT

Transconnector devices and methods of use are provided. A transconnector device has the capability of connecting to elongate spinal fixation elements having various cross-sectional dimensions. The transconnector device is adjustable in three degrees of freedom and is curved to ensure that it maintains a minimum distance posterior of the dura when it is fixed to elongate spinal fixation elements.

16 Claims, 8 Drawing Sheets

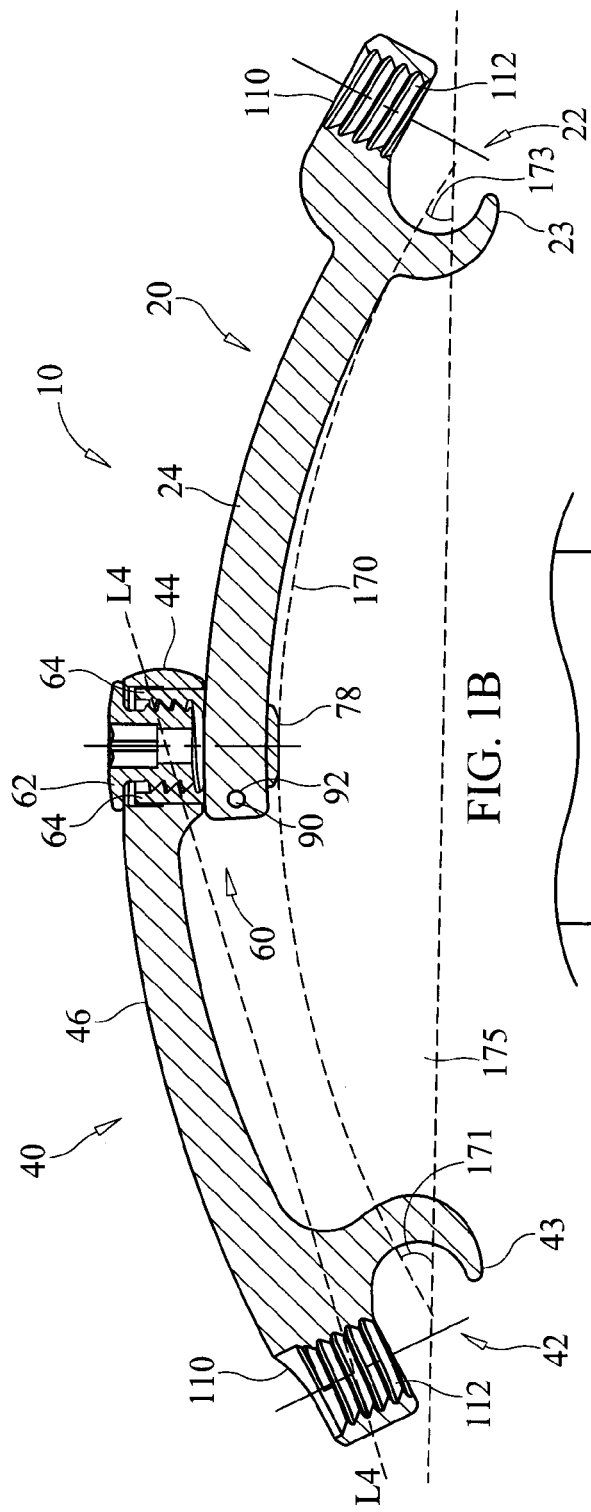
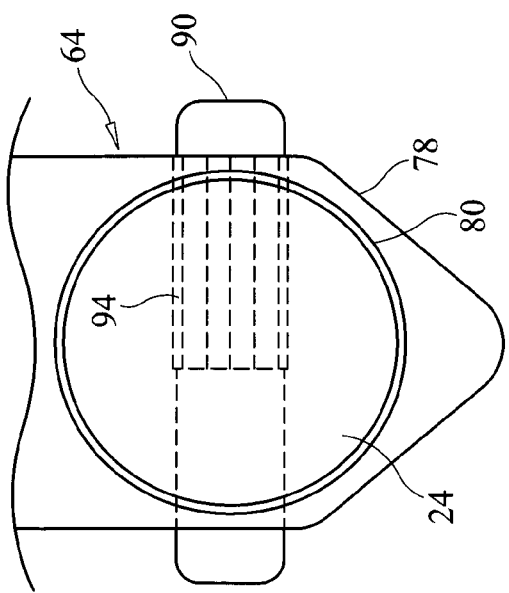
FIG. 1B
FIG. 1C

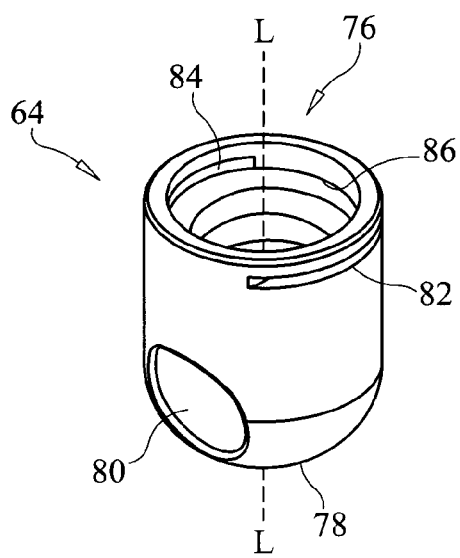
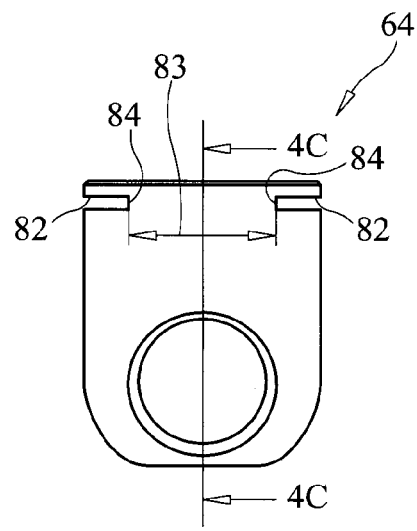
FIG. 4A  FIG. 4B
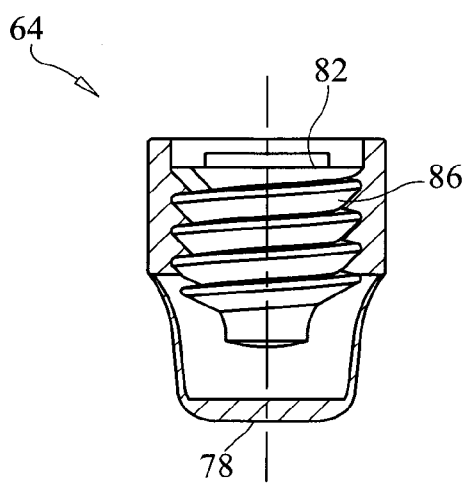
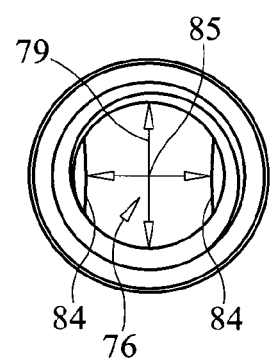
FIG. 4C  FIG. 4D

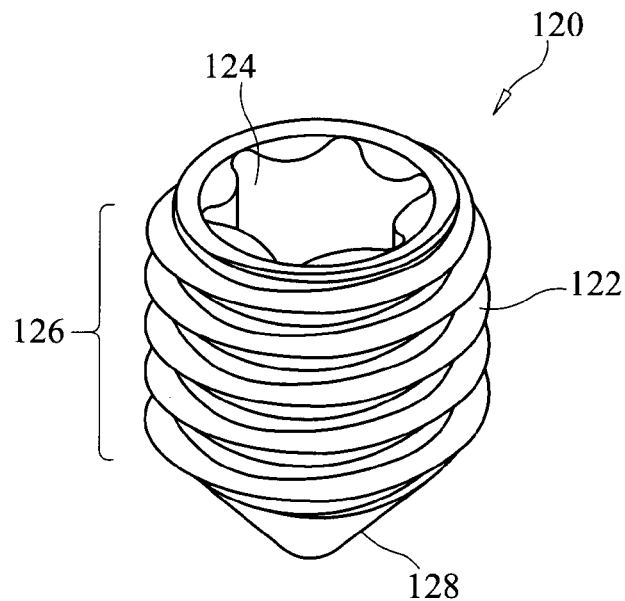
FIG. 6A
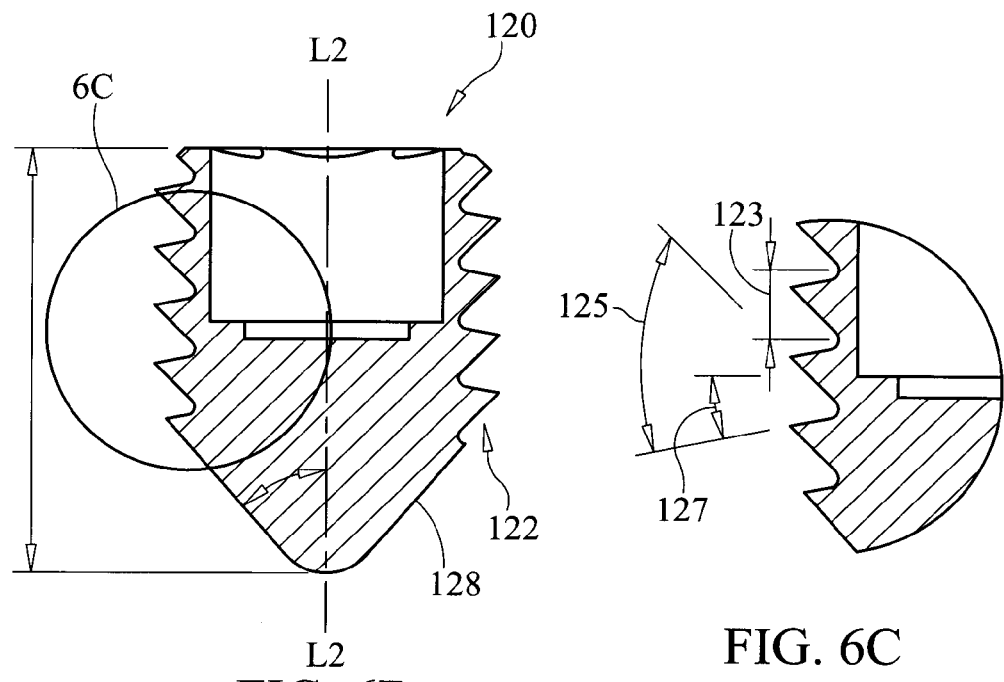
FIG. 6B
FIG. 6C

TRANSCONNECTOR FOR COUPLING FIRST AND SECOND SPINAL FIXATION ELEMENTS

FIELD OF THE INVENTION

The present invention relates to the field of surgical implants and methods, more particularly to spinal implants and surgical methods of using spinal implants.

BACKGROUND OF THE INVENTION

In the surgical treatment of spinal disorders such as scoliosis, numerous systems for attempting to correct such conditions have been devised. These systems usually include a pair of elongate members, typically either rods or plates, placed posterior-laterally on opposite sides of the vertebral column. Each rod/plate is attached to the spine with various attachment devices, such as pedicle screws, spinous process hooks, sublaminar hooks and pedicle hooks.

The strength and stability of a dual rod or plate assembly can be increased by coupling the two rods or plates with a cross-brace or transconnector which extends across the spine, substantially horizontal/perpendicular to the longitudinal axes of the rods or plate. The simplest situation in which a transconnector can be used occurs when the two rods or plates are geometrically aligned. In this case, the two rods or plates are axially parallel to each other, i.e., there is no rod/plate convergence or divergence between the rods in the medial-lateral direction, over the extent of the lengths of the rods. Also, the rods/plates have the same orientation and are parallel with respect to the coronal plane in the anterior-posterior direction, i.e., the rods/plates are coplanar from a lateral view, and the rods/plates are located at a fixed predetermined distance from one another.

Due to a wide variety of factors, the two rods or plates are rarely geometrically aligned in clinical situations. There are several ways to address variations from geometrical alignment. One way is to bend one or both of the rods or plates to accommodate its fixation by the transconnector. However, bending performed in either of the rods or plates is not always possible to achieve and can adversely affect the fixation thereof to the pedicle screws or hooks, etc. that are fixed to the spine, and can compromise the clinical outcome of the surgery. Furthermore, the bending can also adversely affect the mechanical properties of the rods/plates. Additionally or alternatively, the transconnector can be bent to address the geometrical misalignment of the rods/plates, so that the disturbance to the rod(s)/plate(s) positioning is minimized. However, bending of the transconnector can compromise the mechanical performance of the transconnector.

Adjustable transconnectors designed to adapt for variations from geometrical alignment have been provided. However, these transconnectors are multi-piece systems that can be difficult to assembly and use in the surgical environment. Further, there is no guarantee that this type of transconnector cannot become disassembled, losing one or more pieces, after implantation and closing of the patient. Still further, after such transconnectors are implanted (fixed to the rods/plates) there design does not take into account the spacing necessary to ensure that the implant does not engage the dura.

Adjustable connectors of one-piece design that are currently available do not allow for wide-range adjustments to compensate for all three modes in which there may be variation from geometric alignment: convergence or divergence, non-coplanar rods/plates, and variability on rod separation distances, while, at the same time, maintaining separation from the dura and the spinal cord.

There is a continuing need for transconnectors that are fully adjustable to compensate for all three modes of variation from geometrical alignment of the rods/plates being connected by the transconnector, which transconnectors do not pose a risk of disassembly of multiple parts or pose a challenge of assembling multiple parts, and which transconnectors maintain a safe distance, after implantation, from the dura and spinal cord, regardless of the position of the transconnector, the vertebral level where it is used or the span between the two rods/plates that the transconnector is joined to. The present invention meets at least all of the above needs.

SUMMARY OF THE INVENTION

A transconnector for coupling first and second elongate spinal fixation elements is provided, including: a first member having a first coupling portion configured and dimensioned to receive one of the first and second elongate spinal fixation elements, and a first elongate transconnector member extending from the first coupling; a second member having a second coupling portion configured and dimensioned to receive the other of the first and second elongate spinal fixation elements, and an end portion extending from the second coupling; and a joint assembly joining the first elongate member with the end portion, the joint assembly having a first configuration that allows translation, axial rotation about an axis along which the translation of the first elongate transconnector member occurs and rotation about an axis perpendicular to the axis of the rotation about the translation axis, of the first member relative to the second member. The first coupling portion is provided with a first compression member and the second coupling portion is provided with a second compression member. At least one of the first coupling portion and first compression member and the second coupling portion and second compression member are configured to fix one of the first and second elongate spinal fixation elements received by applying a first compression force thereto when the one of the first and second elongate spinal fixation elements has a first cross-sectional dimension. At least one of the first coupling portion and first compression member and the second coupling portion and second compression member are configured to fix one of the first and second elongate spinal fixation elements received by applying a second compression force greater than the first compression force thereto when the one of the first and second elongate spinal fixation elements has a second cross sectional dimension smaller than the first cross-sectional dimension.

In at least one embodiment, at least one coupling portion is configured to fix an elongate spinal fixation element having a cross-sectional dimension in the range of about 5.5 mm to about 6.1 mm.

In at least one embodiment, the elongate spinal fixation element is a rod and the cross-sectional dimension is a diameter.

In at least one embodiment, at least one coupling portion is configured to fix an elongate spinal fixation element having a cross-sectional dimension in the range of about 5.5 mm to about 6.0 mm.

In at least one embodiment, the elongate spinal fixation element is a rod and the cross-sectional dimension is a diameter.

In at least one embodiment, the end portion comprises an opening extending transversely therethrough, and the joint assembly comprises a rotational member having an open first end and a closed second end aligned along a longitudinal axis of the rotational member. The rotational member further includes a second opening extending transversely through a second end portion of the rotational member, and the rotational member is received in the opening through the end portion of the second member so that the second opening extends at least partially from the second member, wherein the elongate transconnector member passes through the second opening.

In at least one embodiment, a pin extends transversely through a free end portion of the elongate transconnector member. The pin is configured and dimensioned to prevent the elongate transconnector member from being pulled out of the second opening.

In at least one embodiment, an actuator is received in the rotational member. The actuator is configured and dimensioned to be actuated to place the joint assembly in a first configuration that permits the translation, axial rotation about an axis of translation and rotation about an axis perpendicular to the axis of translation, and the actuator is also actuatable to place the joint assembly in a second configuration that prevents the translation, axial rotation about an axis of translation and rotation about an axis perpendicular to the axis of translation.

In at least one embodiment, a locking feature is configured and dimensioned to prevent the actuator from being removed from the rotational member.

In at least one embodiment, the first elongate transconnector member is curved relative to a longitudinal axis of the first member.

In at least one embodiment, the second member comprises a second elongate transconnector member interconnecting the second coupling portion and the an end portion, and the second elongate transconnector member is curved relative to a longitudinal axis of the second member.

A transconnector for coupling first and second elongate spinal fixation elements is provided that includes: a first member having a first coupling portion configured and dimensioned to receive one of the first and second elongate spinal fixation elements, and a first elongate transconnector member extending from the first coupling; a second member having a second coupling portion configured and dimensioned to receive the other of the first and second elongate spinal fixation elements, and an end portion extending from the second coupling; and a joint assembly joining the first elongate member with the end portion, the joint assembly having a first configuration that allows translation, axial rotation about an axis of translation of the first elongate transconnector member and rotation about an axis perpendicular to the axis of translation of the first elongate transconnector member, of the first member relative to the second member. The joint assembly has a single actuator actuatable to place the joint assembly in a first configuration that permits the translation, axial rotation about an axis of translation and rotation about an axis perpendicular to the axis of translation. The single actuator is also actuatable to place the joint assembly in a second configuration that prevents the translation, axial rotation about an axis of translation and rotation about an axis perpendicular to the axis of translation. A first locking member is configured and dimensioned to prevent the first member from disconnecting from the joint assembly. A second locking member is configured and dimensioned to prevent the single actuator from disconnecting from the joint assembly.

In at least one embodiment, the first and second members are curved so that, when the first coupling portion is fixed to the one of the first and second elongate spinal fixation elements and the second coupling portion is fixed to the other of the first and second spinal fixation elements, the joint assembly maintains a position spaced posterior of a dura of the patient and a position more posterior than positions of the first and second coupling portions.

In at least one embodiment, the first coupling portion faces away from the joint assembly and the second coupling portion faces away from the joint assembly.

In at least one embodiment, one of the first and second coupling portions faces away from the joint assembly and the other of the first and second coupling portions faces toward the joint assembly.

A surgical method is provided that includes: attaching a first elongate spinal fixation element along one side of a spinal column of a patient; attaching a second elongate spinal fixation element along an opposite side of the spinal column; contacting a transconnector to the first and second elongate spinal fixation elements, wherein the transconnector comprises a first member having a first coupling portion configured and dimensioned to receive one of the first and second elongate spinal fixation elements, a first elongate transconnector member extending from the first coupling; a second member having a second coupling portion configured and dimensioned to receive the other of the first and second elongate spinal fixation elements, an end portion extending from the second coupling; and a joint assembly joining the first elongate member with the end portion; allowing the transconnector to self adjust as the first and second coupling members receive the first and second elongate spinal fixation members, wherein adjusting movement capabilities include translation, axial rotation about an axis of translation of the first elongate transconnector member and rotation about an axis perpendicular to the axis of translation of the first elongate transconnector member, of the first member relative to the second member; and after the transconnector has self adjusted, locking the joint assembly via actuation of a single actuator, wherein the locking prevents the translation, the axial rotation about an axis of translation and the rotation about an axis perpendicular to the axis of translation.

A surgical method is provided that includes: attaching a first coupling portion of a transconnector device to a first elongate spinal fixation element fixed along one side of a spinal column of a patient; and attaching a second coupling portion of the transconnector device to a second elongate spinal fixation element fixed along an opposite side of the spinal column; wherein the first elongate spinal fixation element, at a location where the first coupling portion is attached has a first cross-sectional dimension and the second elongate spinal fixation element, at a location where the second coupling portion is attached has a second cross-sectional dimension, and wherein the first cross-sectional dimension is greater than the second cross-sectional dimension.

In at least one embodiment, the first cross-sectional dimension is about 6.0 mm and the second cross-sectional dimension is about 5.5 mm.

In at least one embodiment, the first cross-sectional dimension is a first diameter and the second cross-sectional dimension is a second diameter.

A surgical method is provided that includes: detaching a coupling portion of a transconnector device fixed to a first elongate spinal fixation; and attaching the coupling portion of the transconnector device to a second elongate spinal fixation element; wherein the first elongate spinal fixation element, at a location where the coupling portion is detached from has a first cross-sectional dimension and the second elongate spinal fixation element, at a location where the coupling portion is attached to has a second cross-sectional dimension, and wherein the first cross-sectional dimension is less than the second cross-sectional dimension.

These and other advantages and features of the invention will become apparent to those persons skilled in the art upon reading the details of the devices and methods as more fully described below.

BRIEF DESCRIPTION OF THE DRAWINGS

FIG. 1B is a longitudinal sectional view of a transconnector device according to an embodiment of the present invention.

FIG. 1C illustrates a pin inserted through an opening in a member of a transconnector device according to an embodiment of the present invention.

FIG. 4A is a perspective view of a rotational member of a transconnector device according to an embodiment of the present invention.

FIG. 4B is a plan view of the rotational member of FIG. 4A.

FIG. 4C is a longitudinal sectional view taken along 4C-4C of FIG. 4B.

FIG. 4D is a top view of a rotational member of a transconnector device according to an embodiment of the present invention.

FIG. 6A is a perspective view of a compression member of a transconnector device according to an embodiment of the present invention.

FIG. 6B is a longitudinal sectional view of the compression member of FIG. 6A.

FIG. 6C is a detail view taken within circle 6C in FIG. 6B.

DETAILED DESCRIPTION OF THE INVENTION

Figure 1A:
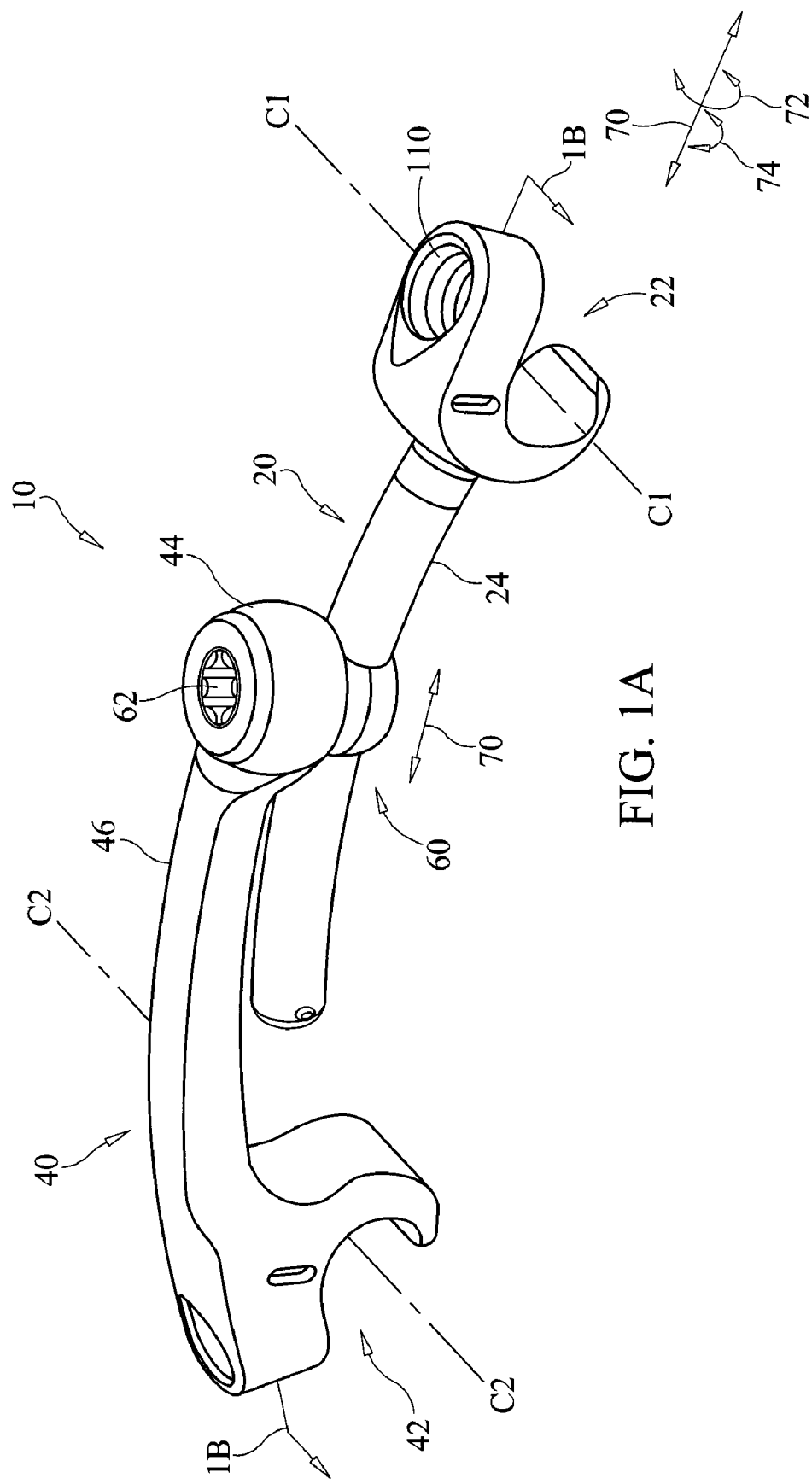
FIG. 1A is a perspective view of a transconnector device according to an embodiment of the present invention.

Before the present devices and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a screw" includes a plurality of such screws and reference to "the rod" includes reference to one or more rods and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Referring now to the drawings in detail, FIG. 1 shows a transconnector device 10 according to an embodiment of the present invention. Transconnector 10 is configured and dimensioned for coupling first and second elongated spinal fixation elements having been attached posterior-laterally to opposite sides of the spinal column. Transconnector device 10 can be made from any suitable biocompatible, rigid materials typically used in orthopedic implant devices, such as titanium, titanium alloy, stainless steel, or other biocompatible, rigid metal. Most components of device 10 (with the possible exception of pin 90) may alternatively be made from rigid polymer or polymer composite such as carbon fibers-filled polyetheretherketone (PEEK). Preferably, at least the portions of transconnector that make contact with the elongated spinal fixation elements are made of the same material as used to make the elongated spinal fixation elements or from implant grade, inert, polymer or polymer composite to avoid galvanic corrosion. The first and second elongate spinal fixation elements that can be joined by transconnector 10 can be cylindrical rods, rectangular bars, plates, or any other device suitable for spinal fusion. As noted, in use, the first elongate spinal fixation element extends along one side of the vertebral column and the second elongate spinal fixation element extends along the other side of the vertebral column. A wide variety of attachment devices such as hooks, screws and clamps can be used to attach the first and second elongate spinal fixation elements to the spine.

Transconnector 10 includes a first member 20 having a first coupling portion 22 configured and dimensioned to receive one of the first and second elongate spinal fixation elements. A first elongate transconnector member 24 extends from the first coupling portion 22.

A second member 40 of the transconnector 10 includes a second coupling portion 42 configured and dimensioned to receive the other of the first and second elongate spinal fixation elements. The second member 40 is further provided with an end portion 44 extending from the second coupling portion 42. A second elongate transconnector member 46 interconnects the second coupling portion 42 and the end portion 44. In alternative embodiments, the first and second elongate transconnector members 24 and 46 may be made shorter or longer than those provided in the embodiment of FIG. 1A, to provide varying ranges of adjustability for distances between the first and second elongate spinal fixation elements. For example, the distance/space between elongate spinal fixation elements will typically be less where attached to the thoracic portion of the spine compared to the distance/space between elongate spinal fixation elements where attached to the lumbar portion of the spine. Additionally, even spaces in the same relative spinal location will vary from patient to patient, particularly when comparing children to adults and females to males. Thus, in addition to the adjustability provided by each individual transconnector 10, sets of transconnectors 10 having first and/or second elongate transconnector members, 24, 46 of varying length are provided to even further extend the ranges of distances between elongate spinal fixation elements that can be coupled to.

Transconnector 10 further includes a joint assembly 60 that connects first elongate member 24 with end portion 44. By turning actuator 62 in one rotational direction, the joint assembly 60 can be placed in a first configuration that allows translation (i.e., along the directions shown by arrow 70 in FIG. 1A), axial rotation about an axis along which the translation of the first elongate transconnector member 24 occurs (in the directions shown by arrow 72 in FIG. 1A) and rotation about an axis perpendicular to the axis of rotation about the translation axis (in the directions shown by arrow 74 in FIG. 1A). By turning actuator 62 in the opposite rotational direction, the joint assembly 60 can be placed in a locked configuration that prevents translation, axial rotation about the axis along which the translation of the first elongate transconnector member 24 occurs and rotation about the axis perpendicular to the axis of rotation about the translation axis.

As shown in the longitudinal sectional view of transconnector 10 in FIG. 1B, joint assembly 60 includes a rotational member 64 that is inserted into an opening 48 of second member 40. Opening 48 extends transversely through the end portion 44 of second member 40 (e.g. see FIG. 3). An actuator 62 such as a cap screw or other threaded actuator is turned into an open end 76 of rotational member 64 having mating threads, as shown in FIG. 1B. In addition to the open end 76 (see FIG. 4A) of rotational member 64, rotational member 64 has a closed end 78. Opening/open end 76 and closed end 78 are aligned with the longitudinal axis L-L of rotational member 64, as shown in FIG. 4A. Rotational member 64 further includes a second opening 80 extending transversely through the side walls of a second end portion of the rotational member, wherein the second end portion is near the closed end 78, as shown in FIG. 4A.

As noted above, rotational member 64 is received in opening 48 and actuator 62 is threaded into open end 76. Additionally, at least a portion of second opening 80 extends the second member 40 and first elongate transconnector member 24 passes through the second opening 80 as shown in FIGS. 1A-1B. A locking feature 90 is provided to prevent the first elongate transconnector member 24 from being completely removed out of the opening 80 of rotational member 64. This greatly simplifies the use of the transconnector 10 during a surgical procedure, as personnel are not required to assemble the transconnector device 10. This also function as a safety feature, as there is substantially no risk of member 20 becoming disconnected from joint 60 and member 40.

In the embodiment shown in FIGS. 1A-1B, the locking feature comprises a pin 90 that passes transversely through and is fixed with respect to the end portion of first elongate transconnector member 24. Pin 90 may be press fit through a transverse opening 92 through member 24, or otherwise fixed in position so that opposite ends of pin 90 extend from opposite sides of opening 92/member 24. Pin 90 may include surface roughness 94 such as knurling or the like, to increase friction between pin 90 and member 24 when pin 90 is fixed by a press fit/friction fit. Pin 90 has a length that is greater than the diameter of opening 80, so that the ends that protrude from both sides of the member 24 cannot pass through the opening 80, as illustrated in FIG. 1C. Thus, elongate member 24 is prevented from being pulled completely out of opening 80 and prevented from being disconnected from rotational member 64.

FIG. 4B is an elevation view of rotational member 64, FIG. 4C is a longitudinal sectional view taken along 4C-4C in FIG. 4B, and FIG. 4D is a top view of the rotational member 64 of FIG. 4A. As shown in FIGS. 4B and 4C, the outside walls of rotational member 64 include recessed or slotted portions 82, which form shoulders or ledges 84 protruding in from the inner walls of rotational member, as shown in FIG. 4A. Shoulders/ledges 84 may be deformed inwardly by compressing the slotted portions 82 together using pliers, pinchers or other type of compression tool. FIG. 4B illustrates shoulder/ledges 84 in an undeformed configuration, where the distance between the shoulders/ledges 84 is represented by 83. FIG. 4D illustrates shoulder/ledges 84 in a deformed configuration, where the distance between the shoulders/ledges 84 is represented by 85 and where distance 85 is less than distance 83.

Figure 5A:
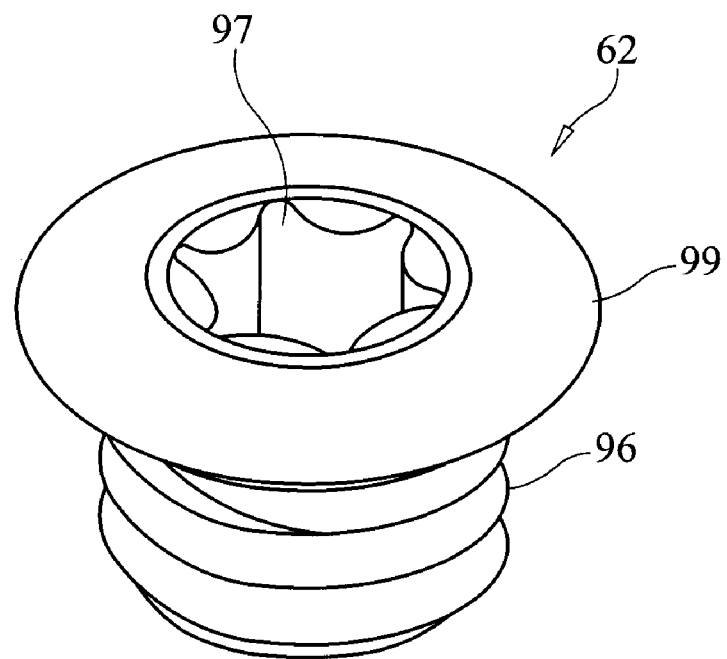
FIG. 5A is a perspective view of an actuator of a transconnector device according to an embodiment of the present invention.
Figure 5B:
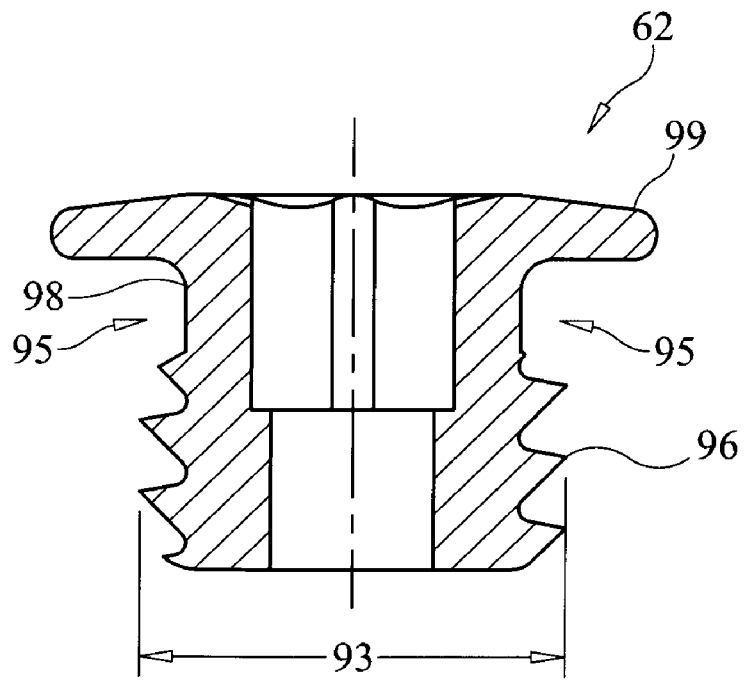
FIG. 5B is a longitudinal sectional view of the actuator of FIG. 5A.

As noted previously, the longitudinally oriented opening which opening 76 leads into is provided with threads 86 that mate with thread 96 of actuator 62. The largest outside diameter of threads 96 is shown as 93 in FIG. 5B. Distance 93 is greater than distance 85 but less than distance 83. Actuator 62 further includes a head 99 that has an outside diameter that is greater than the inside diameter 79 of opening 76. A neck portion 98 is formed between head 99 and threads 96. Neck portion 98 has an outside diameter 95 that is less than distance 85. Upon assembly (note that joint assembly 60 is completely assembled prior to receipt by the surgeon or other end user), actuator 62 is threaded into rotational member 64 through opening 76 while shoulders/ledges 84 are in the undeformed configuration, being separated by distance 83. Thus, since distance 83 is greater than distance 93, the actuator 62 can be freely threaded into the rotational member. The actuator is threaded in until the top most thread is below the bottom surfaces of the shoulders/ledges 84. Then the shoulders/ledges 84 are deformed by compression of the slotted portion 82 so that shoulders/ledges are only separated by a distance 85. Since distance 85 is less than distance 93, actuator is locked/prevented from being rotated completely out of the rotational member 64 so as to be separated therefrom. This greatly simplifies the use of the transconnector 10 during a surgical procedure, as personnel are not required to assemble the transconnector device 10. This also function as a safety feature, as there is substantially no risk of actuator 62 becoming disconnected from rotational member 64 and device 10.

Neck portion 98 has sufficient length (spacing between bottom surface of head 99 and top-most thread 96) to allow a full range of motion of the actuator 62 turning in the threads 86, to both lock and unlock the joint assembly as described in more detail below. Since the neck portion 98 has an outside diameter 95 less than distance 85, it can rotate and translate freely relative to shoulders/ledges 84 and the actuator 62 is torqued to move up and down relative to rotational member 64.

When loosely assembled, in an unlocked configuration, first elongate transconnector member 24 can rotate within and relative to opening 80 of rotational member 64. Thus, if one of the elongate spinal fixation elements at a location to be joined by device 10 has a longitudinal axis that extends at an angle $\alpha_1$ relative to the coronal plane of the patient (i.e., the plane which divides the body in half from front to back) and the other of the elongate spinal fixation elements at a location to be joined by device 10 has a longitudinal axis that extends at an angle $\alpha_2$ relative to the coronal plane of the patient, then relative rotation of components 40 and 20 can take place in direction 72 to adjust the axes $C_1$ and $C_2$ to be collinear with (i.e., at angles $\alpha_1$ and $\alpha_2$ to the coronal plane respectively) the respective elongate spinal fixation elements to be coupled to. This allows the coupling members 22, 42 to be coupled to the elongate spinal fixation elements without the need to bend either fixation element or the transconnector 10.

Additionally, first elongate transconnector member 24 can be pushed or pulled (translated) through opening 80 to either decrease or increase the distance between members 22 and 42, respectively. This feature allows the transconnector 10 to be readily adjusted for different patient anatomies (sizes) and used in different regions of the spine. For example, the lumbar vertebrae are typically larger than the thoracic vertebrae, As a result, the distance between fixation elements in the lumbar region would be greater than the distance between the fixation elements in the thoracic regions. Because the length of the first elongate transconnector member 24 that extends through and beyond opening 80 of rotational member 64 can be changed, the transconnector 10 can be adjusted for use in different spinal regions without the need to bend either fixation element or the transconnector 10. As noted above, in order to further increase the adjustability of the transconnector 10, the length of one or both of the first and second elongate transconnector members 24, 46 can be manufactured in different sizes.

Still further, rotational member 64 can rotate within opening 48 to allow a change in the angle between first elongate transconnector member 24 and second elongate transconnector member 46 in a plane perpendicular to the longitudinal axis L-L of rotational member 64.

Actuator 62 can be torqued to draw the rotational member 64 further up into the end portion 44/48. This can be continued until member 24 is drawn against the bottom surface of end portion 44 with sufficient compression force to prevent member 24 from any ability to translate or rotate in any of the directions previously described, i.e., to immobilize member 24 relative to member 46. Likewise, this also prevents rotational member 62 from rotating, as it is locked in position relative to end member 44. A tool interface 97 is formed into the top face of the head 99, see FIG. 5A, for receiving the working end of a driving tool used to turn the actuator 62.

The structure of the coupling portions 22, 42 will depend on the structure of the elongate spinal fixation elements to be coupled to. For example, if the elongate spinal fixation elements are elongate plates, then coupling portions 22, 42 are configured and dimensioned to receive and clamp elongate plates, by providing the coupling portions with a shape that mates with the elongate plates, such as channel-shaped clamps, for example. As another example, if the elongate spinal fixation elements are elongate cylindrical rods, then coupling portions 22, 42 are each provided with a hook shape, as illustrated in the figures. The coupling portions 22, 42 further each include a threaded hole 110 (FIGS. 1A-1B and 2-3) and a compression member 120 (FIG. 6A) having threads 122 that mate with threads 112 of coupling portions 22, 42. In the embodiment shown in FIG. 6A, compression member 120 comprises a set screw.

Threads 122 and compression member 120, as well as threads 112 are dimensioned and configured so that coupling portions 22, 42 can couple to rods having varying diameters, such as rods having diameters in the range of about 5.5 mm to about 6.1 mm, typically in the range of about 5.5 mm to about 6.0 mm. Likewise, if coupling portions are configured to couple to elongate elements other than rods, coupling portions are configured and dimensioned to couple to elements having cross-sectional dimensions in the range of about 5.5 mm to about 6.1 mm, typically in the range of about 5.5 mm to about 6.0 mm.

As best seen in FIG. 6A, compression member 120 has a first end with a tool interface 124 formed therein for receiving the working end of a driving tool used to turn the compression member 120, a threaded cylindrical first body portion 126 and a tapered (typically, conically tapered) second body portion 128. The curved portion of each coupling portion 22, 42 has a radius of curvature that is greater than a radius of curvature of an elongate spinal fixation element to be coupled to. As a result, the only contact between coupling portion 22, 42 and the fixation elements 150, 150' is at a region near the tip portion 23, 43 (see FIGS. 1B, 7A and 7B). Furthermore, the only contact between compression member 120 and the fixation element 150, 150' is on the tapered second body portion 128 (see FIGS. 7A-7B). Thus, the fixation elements are clamped between the second body portion 128 and the curved region of coupling portion 22, 42 near the tip portion 23, 43.

As noted, device 10 is configured and dimensioned to couple to elongate spinal fixation elements of varying cross-sectional dimensions. It is noted that, in order to successfully couple (clamp to and fix to prevent relative motion between coupling portion and elongate spinal fixation element) coupling portion 22, 42 to an elongate spinal fixation element 150, 150', there is a minimal threshold amount of compression that must be applied to fixation element 150, 150' by coupling portion 22, 42 (i.e., between the curved surface of coupling portion 22, 42 and the tapered portion 128 of compression member 120). It is further noted that the minimal threshold amount of compression required increases as the cross-sectional dimension of the elongate spinal fixation element decreases. Accordingly, the threads 112 and 122 must be designed to accommodate the increase in forces required for fixing a relatively smaller (cross sectional dimension) fixation element as well as a fixation element having a relatively larger cross-sectional dimension. The decision to use a particular rod/plate size/system can be made or changed intra-operatively. For example, a surgeon may change a 5.5 mm rod to be implanted and decide to rather us a 6.0 mm rod if correction of a rigid scoliosis condition cannot be maintained by 5.5 mm rods. In this case, the surgeon would not need to change out transconnector devices 10, as devices 10 can couple to 6.6 mm rods as well as to 5.5 mm rods, as noted. Likewise, for surgical revisions, a surgeon may want to change one or more elongate spinal fixation elements to element(s) having a different cross-section dimension. When changing from a 5.5 mm cross-sectional dimension to a 6.0 mm cross-section dimension, or vice versa, of either one or both elongate spinal fixation elements, any transconnector devices 10 used to join the original elongate spinal fixation elements would also be capable of joining the new arrangements of elongate spinal fixation elements.

As another example, there are situations where a surgeon needs to extend the results of a fusion procedure previously performed, whether the extension is placed either superiorly or inferiorly (or both) of the original elongate spinal fixation elements to correct a secondary or compensatory deformity that has developed after the original fusion procedure was performed. In many of these cases different diameter rods (or plates or other elongate members having a different cross-sectional dimension) are used to extend the original construct. Due to the particular anatomy of a patient's spine, the type of deformity/pathology and/or difficulty in inserting a rod-to-rod connector at a particular side/level, the surgeon may need to connect the elongate spinal fixation elements at a different level on one side than at the level connected to on the other side. In such a situation, two different elongate spinal fixation element sizes may be present in the same vertebral level. In this case, transconnector 10 can be used to connect the elongate spinal fixation elements at that vertebral level, for example, when one elongate spinal fixation element has a cross-sectional dimension of about 5.5 mm and the other elongate spinal fixation element has a cross-sectional dimension of about 6.0 mm.

In still another application of the present invention, although not performed as frequently today, surgeons would previously attempt to correct some spinal deformities by implanting one elongate spinal fixation element only, and would revise these cases later if needed. Historically, revisions of such cases have frequently been needed. In a case of this type, if a surgeon is provided with transconnectors 10 of the present invention, the surgeon may decide to leave the original elongate spinal fixation element in place and add a second elongate spinal fixation element on the other side of the vertebrae, and the second elongate spinal fixation element may have a different cross-sectional dimension than that of the first elongate spinal fixation element. Transconnector 10 could then be used to couple to both the first and second elongate spinal fixation elements. As one example, the first elongate spinal fixation element could be a rod having a diameter of about 5.5 mm and the second spinal fixation element could be a rod having a diameter of about 6.0 mm.

Figure 7A:
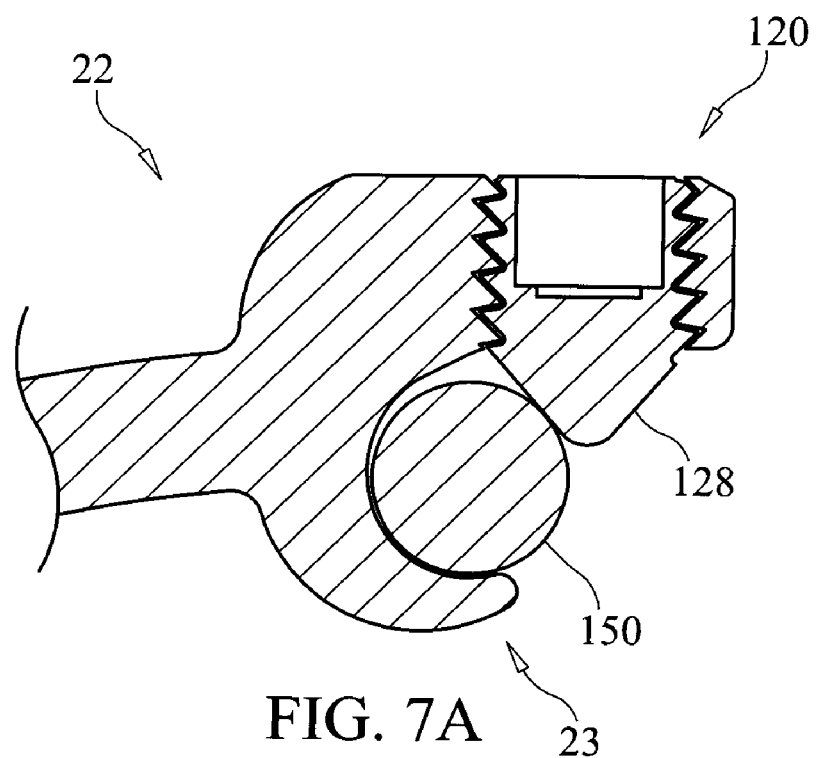
FIG. 7A is a partial sectional view of a coupling portion of a transconnector device fixed to an elongate spinal fixation element having a first cross-sectional dimension.
Figure 7B:
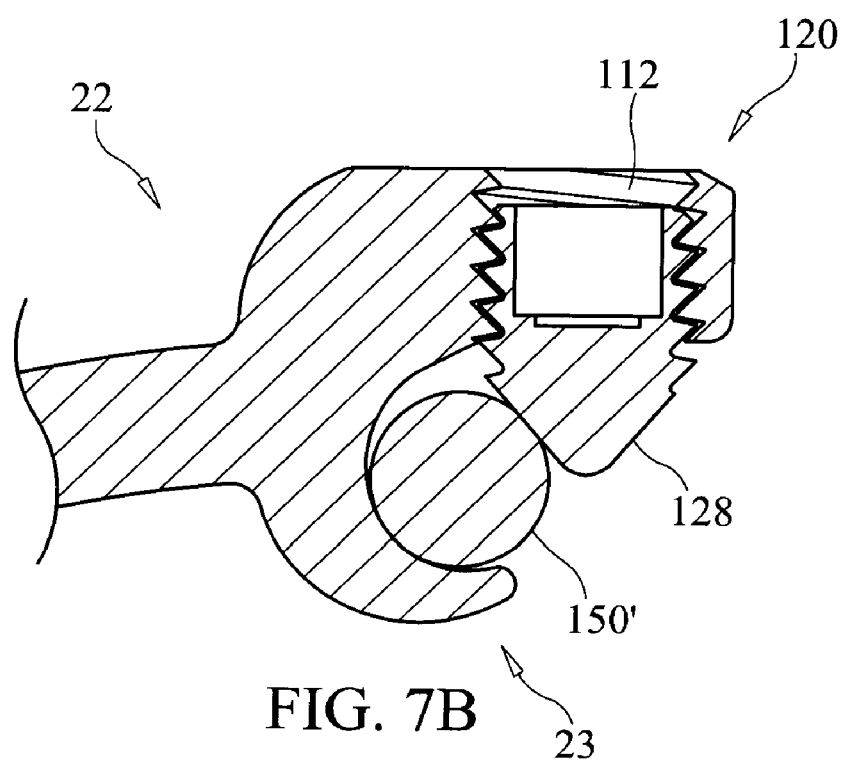
FIG. 7B a partial sectional view of the coupling portion of FIG. 7A fixed to a second elongate spinal fixation element having a second cross-sectional dimension less than the first cross-sectional dimension of the first element illustrated in FIG. 7A.

For example, in the embodiment shown in FIG. 7A, the coupling portion 22 and compression member 120 are designed to couple to an elongate spinal fixation element 150 having a diameter of about 6 mm. It is noted that although the examples shown in FIGS. 7A-7B are illustrated using coupling portion 22, that this disclosure applies equally to use of coupling portion 42. Accordingly, when coupling portion 22 has been coupled to element 150 with sufficient compression force (e.g., about 8.0 Nm to fix the components together with sufficient force required to prevent relative movements therebetween during use, the end of the compression member 120 having the tool interface 124 is flush with the coupling portion 22, see FIG. 7A.

However, with the same embodiment applied to an elongate spinal fixation element 150' having a diameter of about 5.5 mm (see FIG. 7B), when coupling portion 22 has been coupled to element 150' with sufficient compression force to fix the components together with sufficient force required to prevent relative movements therebetween during use, the end of the compression member 120 having the tool interface 124 is recessed within the coupling portion 22, see FIG. 7B. As noted above, the element 150' having the smaller cross-sectional dimension requires a greater compression force to successfully fix to it. In the case of the 5.5 mm rod it has been found that a compression force of at least about 8.5 Nm must be applied. A still further demand is made upon the threads 112, 122 by the fact that the threads of the compression member do not mate with the top thread 112 of the threads 112 of the coupling portion, as shown in FIG. 7B. This also means that a bottom thread 122 of compression member 120 is not engaged with a mating thread 112. Accordingly, the remaining threads 112, 122 that are engaged must withstand additional forces, not only for the increased amount of overall compression that must be applied, but also for the fact that the overall compression forces are divided by a fewer number of mating threads.

Accordingly, the design of a device 10 that can accommodate the coupling to elongate spinal fixation elements having varying cross-sectional dimensions must be provided with robust threads 112, 122 that can accommodate the increased forces that will be applied thereto. In the embodiment shown in FIG. 6B, threads 122 are buttress threads. It is noted that although the examples of threads described here are with regard to threads 122 of the compression member 120, that threads 112 will be correlated to this design features, as they must mate with threads 122. The overall length of compression member 120 in this embodiment is about 7.0 mm to about 7.5 mm, typically about 7.3 mm. The angle 121 of taper of second body portion 128 relative to the longitudinal axis L2-L2 of compression member 120 is about thirty degrees to about sixty degrees, typically about thirty-five to fifty degrees, more typically about forty degrees. The pitch 123 (see detailed illustration in FIG. 6C) of threads 122 (and therefore also of threads 112 is in the range of about 0.7 mm to about 1.2 mm, typically about 1.0 mm. The leading flank angle or thread angle 125 of threads 122 (and also of threads 112) is about forty degrees to about sixty-five degrees, preferably about fifty-five degrees. The trailing flank angle 127 between the top of a buttress thread and the horizontal is about zero degrees to about fifteen degrees, typically about seven degrees. The inside diameter of the threads may be about 4.0 mm and the outside diameter of the threads may be about 6.0 mm In one embodiment, the inside diameter of threads 122 was about 4.5 mm and the outside diameter was about 5.8 mm, although, as noted, each of these diameters may vary.

Figure 2:
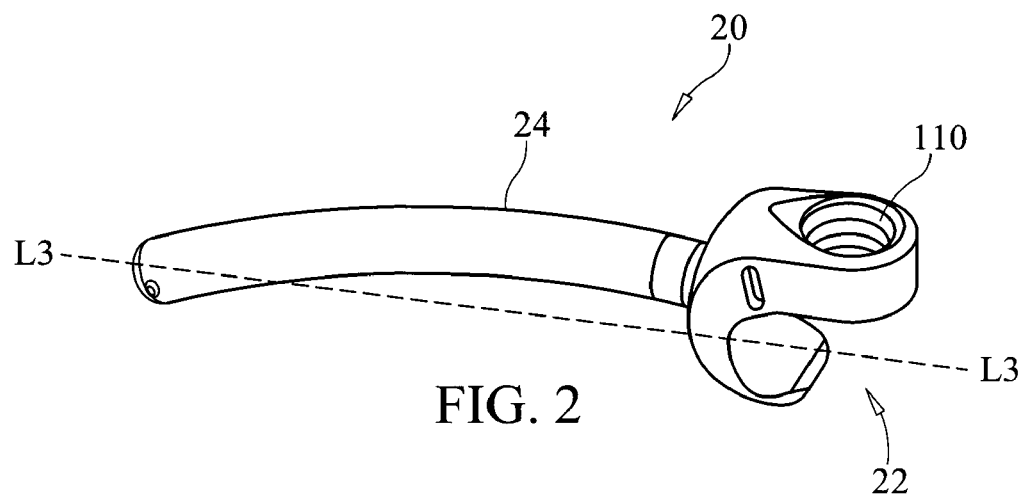
FIG. 2 illustrates a first member of a transconnector device according to an embodiment of the present invention.
Figure 3:
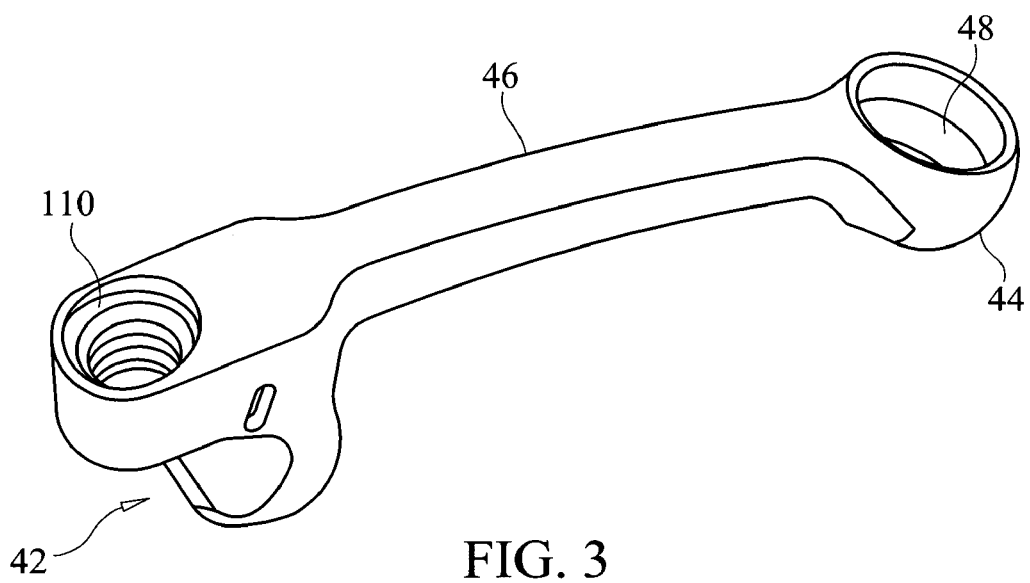
FIG. 3 illustrates a second member of a transconnector device according to an embodiment of the present invention.

Another important feature of transconnector 10 is its curvature relative to the coronal plane when installed in a patient, i.e., coupled to two elongate spinal fixation elements. This curvature 170 (see FIG. 1B) defined by a curved line passing through the centers from which the radii of curvature are measured for the coupling portions 22 and 42, and intersecting the bottom most point of the closed end 78 of rotational member 64, is sufficient to ensure that the bottom end 78 of rotation member does not contact the dura once device 10 has been installed. Preferably, the radii of curvature are designed so that the bottom end 78 is never less than about 12.0 mm above the dura when installed in any configuration that the device is capable of being placed in. In order to accomplish this, first elongate transconnector member 24 is curved, relative to the longitudinal axis L3-L3 of first member 20, as shown in FIG. 2. This curvature can range from about thirty degrees to about seventy degrees, and is typically in the range of about forty-five degrees and about 64.5 degrees. Likewise, second elongate transconnector member 46 can be curved, relative to the longitudinal axis L4-L4 of second member 40, as shown in FIGS. 1B and 3. This curvature can range from about thirty degrees to about fifty degrees, and is typically in the range of about 30.7 degrees to about 53.9 degrees. The curvature 170 will vary depending upon the span (distance) between 22 and 42, and results from the specific radii of curvature of members 20 and 40. Preferably, the angles 171, 173 where the line of curvature 170 intersects the horizontal line 175 (e.g., see FIG. 1B) are never less than about thirty degrees and are typically in the range of about thirty degrees to about sixty degrees.

Figure 8:
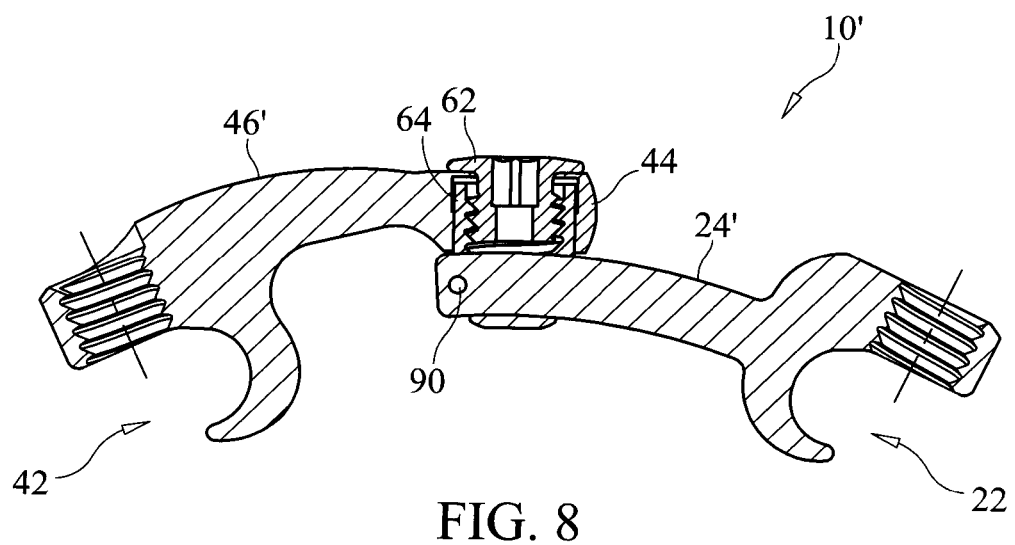
FIG. 8 is a longitudinal sectional view of a transconnector device according to another embodiment of the present invention.

FIG. 8 is a longitudinal sectional view of a transconnector device 10' according to another embodiment of the present invention. This embodiment is configured to couple to elongate spinal fixation elements that are separated by a shorter distance (inter-fixation element distance), relative to the inter-fixation element distances that the device 10 of FIGS. 1A-1B is designed for. Accordingly, all elements are substantially the same as in transconnector 10 except for the first and second elongate transconnector elements 24', 46', which are shorter than the respective elements 24, 46.

Figure 9:
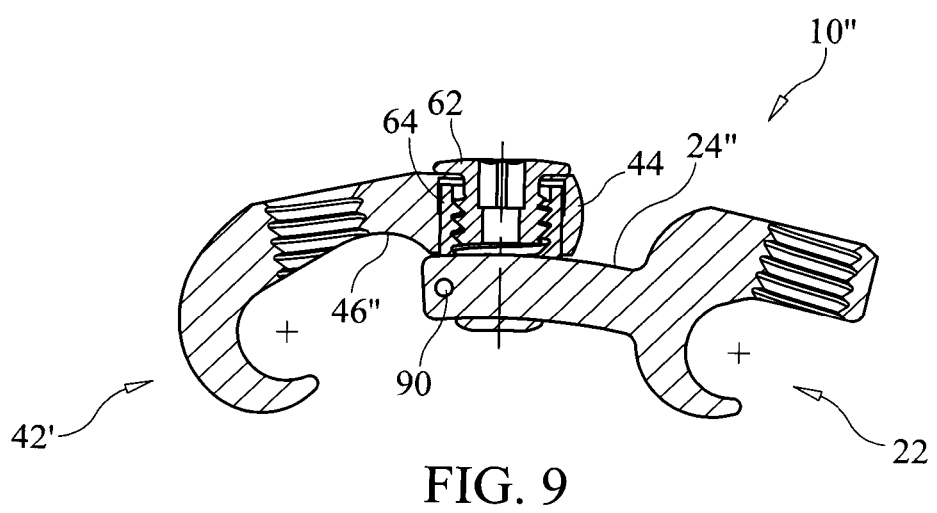
FIG. 9 is a longitudinal sectional view of a transconnector device according to another embodiment of the present invention.

The embodiment of FIG. 9 is configured and dimensioned to couple with elongate spinal fixation elements having an even smaller range of inter-fixation element distances than those for which the embodiment of FIG. 8 is designed for. In this regard, the first and second elongate transconnector elements 24", 46" are shorter than the respective elements 24', 46'. Another difference in transconnector 10" from the transconnectors 10 and 10' of FIGS. 1B and 8, is that both coupling portions 22, 42 of device 10 and both coupling portions 22, 42 of device 10' faces away from the joint assembly 60. That is, the openings of the hook portions of coupling portions 22, 42 face away from the center of the device, i.e., away from the joint assembly 60. In the device 10" of FIG. 9, however, one of the hooks (in FIG. 9, it is the hook of coupling portion 42) faces toward the joint assembly 60 while the other of the hooks faces away from the joint assembly. Alternative to the arrangement shown in FIG. 9, the hook of portion 22 could face toward the joint assembly and the hook of portion 42 could face away from the joint assembly. In either of these arrangements, this allows the device 10" to be installed into a relatively smaller inter-fixation element distance than would be possible with a device having all the same components as device 10" but where both hook portions face away from the joint assembly.

All of the embodiments described herein simplify methods of implantation by the surgeon relative to prior art transconnectors. The fact that the devices 10, 10', 10" are preassembled and cannot be accidentally disassembled relieves and requirement of assembling the device by the surgical team, and ensures that the device remains integrated during the implantation procedure.

One the elongate spinal fixation elements have been successfully implanted according to any known techniques currently used for such implantation, device 10, 10' or 10", is next installed. Additionally, the device is in the configuration where translation and the two degrees of rotation described above are permitted. Accordingly, the surgeon can then place one of the coupling portions to receive one of the elongate spinal fixation elements, and place the other one of the coupling portions to receive the other of the elongate spinal fixation elements. Optionally, the compression members 120 can be turned into the portions 22, 42 to snugly contact the spinal fixation elements at this time, but they are not yet torqued down to perform the fixation. The ability to translate the first and second members 20, 40 relative to one another allows adjustment of the inter-fixation element distance, while the relative rotatability of the first and second members allows the coupling portions 22, 42 to be readily fitted to the fixation elements, without the need to bend the fixation elements or the transconnector device. Accordingly, the transconnector device is allowed to "self-adjust" via these translation and rotation movements responsive to contacting the coupling portions to receive the elongate fixation elements. Once the coupling portions have been fitted to the fixation elements (and optionally "snugged" in place), actuator 62 is next torqued down to lock the transconnector in the appropriate configuration and prevent any further translations or rotations of first member 20 relate to second member 40. Then the coupling members 22, 42 are fixed to the fixation elements, by torquing compression members 120 to at least the minimum threshold compression force required to complete the fixation. This completes the installation of the transconnector to the fixation elements.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A transconnector for coupling first and second elongate spinal fixation elements, said transconnector comprising:
   a first member having a first coupling portion configured and dimensioned to receive one of said first and second elongate spinal fixation elements, and a first elongate transconnector member extending from said first coupling portion;
   a second member having a second coupling portion configured and dimensioned to receive the other of said first and second elongate spinal fixation elements, and an end portion extending from said second coupling portion; and
   a joint assembly joining said first elongate transconnector member with said end portion, said joint assembly having a first configuration that allows translation, axial rotation about an axis along which said translation of said first elongate transconnector member occurs and rotation about an axis perpendicular to said axis of said rotation about the translation axis, of said first member relative to said second member;
   said first coupling portion provided with a first compression member and said second coupling portion provided with a second compression member;
   wherein said end portion comprises an opening extending transversely therethrough, and said joint assembly comprises a rotational member having an open first end and a closed second end aligned along a longitudinal axis of said rotational member, said rotational member further comprising a second opening extending transversely through a second end portion of said rotational member, and wherein said rotational member is received in said opening through said end portion of said second member so that said second opening extends at least partially from said second member, and wherein said elongate transconnector member passes through said second opening;
   an actuator received in said rotational member, said actuator being configured and dimensioned to be actuated to place said joint assembly in a first configuration that permits said translation, axial rotation about an axis of translation and rotation about an axis perpendicular to said axis of translation, and wherein said actuator is actuatable to place said joint assembly in a second configuration that prevents said translation, axial rotation about an axis of translation and rotation about an axis perpendicular to said axis of translation; and a locking feature configured and dimensioned to prevent said actuator from being removed from said rotational member.

2. The transconnector of claim 1, wherein said at least one coupling portion is configured to fix an elongate spinal fixation element having a cross-sectional dimension in the range of about 5.5 mm to about 6.1 mm.

3. The transconnector of claim 2, wherein said at least one coupling portion is configured to fix an elongate spinal fixation element having a cross-sectional dimension in the range of about 5.5 mm to about 6.0 mm.

4. The transconnector of claim 3, wherein said elongate spinal fixation element is a rod and said cross-sectional dimension is a diameter.

5. The transconnector of claim 1, wherein said elongate spinal fixation element is a rod and said cross-sectional dimension is a diameter.

6. The transconnector of claim 1, further comprising a pin extending transversely through a free end portion of said elongate transconnector member, said pin being configured and dimensioned to prevent said elongated transconnector member from being pulled out of said second opening.

7. The transconnector of claim 1, wherein said first elongate transconnector member is curved relative to a longitudinal axis of said first member.

8. The transconnector of claim 7, wherein said second member comprises a second elongate transconnector member interconnecting said second coupling portion and said end portion, and wherein said second elongate transconnector member is curved relative to a longitudinal axis of said second member.

9. A transconnector for coupling first and second elongate spinal fixation elements, said transconnector comprising:
    a first member having a first coupling portion configured and dimensioned to receive one of said first and second elongate spinal fixation elements, and a first elongate transconnector member extending from said first coupling portion;
    a second member having a second coupling portion configured and dimensioned to receive the other of said first and second elongate spinal fixation elements, and an end portion extending from said second coupling portion; and
    a joint assembly joining said first elongate transconnector member with said end portion, said joint assembly having a first configuration that allows translation, axial rotation about an axis of translation of said first elongate transconnector member and rotation about an axis perpendicular to said axis of translation of said first elongate transconnector member, of said first member relative to said second member;
    said joint assembly comprising a single actuator actuatable to place said joint assembly in a first configuration that permits said translation, axial rotation about an axis of translation and rotation about an axis perpendicular to said axis of translation, and wherein said single actuator is actuatable to place said joint assembly in a second configuration that prevents said translation, axial rotation about an axis of translation and rotation about an axis perpendicular to said axis of translation;
    a first locking member configured and dimensioned to prevent said first member from disconnecting from said joint assembly; and
    a second locking member configured and dimensioned to prevent said single actuator from disconnecting from said joint assembly, regardless of whether said joint assembly is in said first configuration or said second configuration.

10. The transconnector of claim 9, wherein said first and second members are curved so that, when said first coupling portion is fixed to said one of said first and second elongate spinal fixation elements and said second coupling portion is fixed to the other of said first and second spinal fixation elements, said joint assembly is adapted to maintain a position spaced posterior of a dura of a patient and a position more posterior than positions of said first and second coupling portions.

11. The transconnector of claim 9, wherein said first coupling portion faces away from said joint assembly and said second coupling portion faces away from said joint assembly.

12. The transconnector of claim 9, wherein said one of said first and second coupling portions faces away from said joint assembly and the other of said first and second coupling portions faces toward said joint assembly.

13. A transconnector for coupling first and second elongate spinal fixation elements, said transconnector comprising:
    a first member having a first coupling portion configured and dimensioned to receive one of said first and second elongate spinal fixation elements, and a first elongate transconnector member extending from said first coupling portion;
    a second member having a second coupling portion configured and dimensioned to receive the other of said first and second elongate spinal fixation elements, and an end portion extending from said second coupling portion and having an opening extending transversely therethrough; and
    a joint assembly joining said first elongate transconnector member with said end portion, said joint assembly including a rotational member having an open first end and a closed second end aligned along a longitudinal axis of said rotational member, said rotational member further comprising a second opening extending transversely through a second end portion of said rotational member, and wherein said rotational member is received in said opening through said end portion of said second member so that said second opening extends at least partially from said second member, and wherein said elongate transconnector member passes through said second opening; an actuator having a shaft portion received in said rotational member and a head portion extending transversely to said shaft portion, said actuator being configured and dimensioned to be actuated to place said joint assembly in a first configuration that permits said translation, axial rotation about an axis of translation and rotation about an axis perpendicular to said axis of translation, and wherein said actuator is actuatable to place said joint assembly in a second configuration that prevents said translation, axial rotation about an axis of translation and rotation about an axis perpendicular to said axis of translation; and
    said head portion extending for a first distance along a direction of a longitudinal axis of said shaft portion, and said shaft portion extending for a second distance along said direction of said longitudinal axis of said shaft portion, wherein said second distance is greater than said first distance.

14. The transconnector of claim 13, further comprising a locking feature configured and dimensioned to prevent said actuator from being removed from said rotational member.

15. A transconnector assembly comprising:
a first member having a first coupling portion and a first elongate transconnector member extending from said first coupling portion;
a second member having a second coupling portion and an end portion extending from said second coupling portion;
a joint assembly joining said first elongate transconnector member with said end portion, said joint assembly having a first configuration that allows translation, axial rotation about an axis along which said translation of said first elongate transconnector member occurs and rotation about an axis perpendicular to said axis of said rotation about the translation axis, of said first member relative to said second member;
said first coupling portion provided with a first compression member and said second coupling portion provided with a second compression member;
said first coupling portion and first compression member fixed to a first elongate spinal fixation element;
said second coupling portion and second compression member fixed to a second elongate spinal fixation element;
wherein said first elongate spinal fixation element has a first cross-section dimension in a location fixed by said first coupling portion and first compression member and said second elongate spinal fixation element has a second cross-section dimension in a location fixed by said second coupling portion and second compression member; and
wherein said second cross-section dimension is greater than said first cross-section dimension.

16. The transconnector assembly of claim 15, wherein said second cross-section dimension is about 6.0 mm and said first cross-section dimension is about 5.5 mm.

* * * * *

UNITED STATES PATENT AND TRADEMARK OFFICE
CERTIFICATE OF CORRECTION

PATENT NO. : 8,221,466 B2
APPLICATION NO. : 12/646571
DATED : July 17, 2012
INVENTOR(S) : Asaad Page 1 of 1

It is certified that error appears in the above-identified patent and that said Letters Patent is hereby corrected as shown below:

Column 13, Line 43 please delete "and" and insert --any--;
Column 13, Line 44 please delete "One" and insert --Once-- and;
Column 14, Line 5 please delete "relate" and insert --relative--.

Signed and Sealed this
Twelfth Day of March, 2013

Teresa Stanek Rea
*Acting Director of the United States Patent and Trademark Office*